(12) United States Patent
Le Flohic

(10) Patent No.: US 8,927,708 B2
(45) Date of Patent: Jan. 6, 2015

(54) PROCESS FOR THE SYNTHESIS OF 7,8-DIMETHOXY-1,3-DIHYDRO-2H-3-BENZAZEPIN-2-ONE COMPOUNDS, AND APPLICATION IN THE SYNTHESIS OF IVABRADINE

(71) Applicant: Les Laboratoires Servier, Suresnes Cedex (FR)

(72) Inventor: Alexandre Le Flohic, Fauville en Caux (FR)

(73) Assignee: Les Laboratoires Servier, Suresnes Cedex (FR)

( * ) Notice: Subject to any disclaimer, the term of this patent is extended or adjusted under 35 U.S.C. 154(b) by 0 days.

(21) Appl. No.: 14/223,143

(22) Filed: Mar. 24, 2014

(65) Prior Publication Data

US 2014/0296512 A1    Oct. 2, 2014

(30) Foreign Application Priority Data

Mar. 26, 2013  (FR) ...................................... 13 52741

(51) Int. Cl.
*C07D 223/16*   (2006.01)
*C07C 235/34*   (2006.01)

(52) U.S. Cl.
CPC ............ *C07D 223/16* (2013.01); *C07C 235/34* (2013.01)
USPC ....................................................... 540/523

(58) Field of Classification Search
USPC ....................................................... 540/523
See application file for complete search history.

(56) References Cited

U.S. PATENT DOCUMENTS 5,296,482 A    3/1994  Peglion

FOREIGN PATENT DOCUMENTS

EP          0534859       3/1993
WO    WO 2008/066681     6/2008

OTHER PUBLICATIONS

French Search Report for FR1352741 of Nov. 27, 2013.

*Primary Examiner* — Bruck Kifle
(74) *Attorney, Agent, or Firm* — Hueschen and Sage

(57) ABSTRACT

Process for the synthesis of the compound of formula (I):

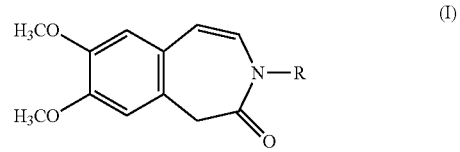

wherein R represents a para-methoxybenzyl (PMB) group or the following group:

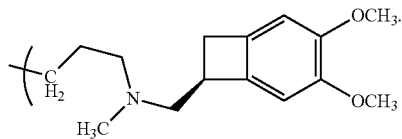

Application in the synthesis of ivabradine and addition salts thereof with a pharmaceutically acceptable acid.

11 Claims, No Drawings

PROCESS FOR THE SYNTHESIS OF 7,8-DIMETHOXY-1,3-DIHYDRO-2H-3-BENZAZEPIN-2-ONE COMPOUNDS, AND APPLICATION IN THE SYNTHESIS OF IVABRADINE

The present invention relates to a process for the synthesis of the compound of formula (I):

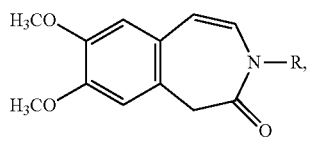
(I)

wherein R represents a para-methoxybenzyl (PMB) group or the following group:

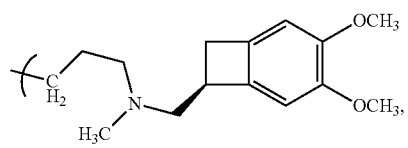 [SMILES: CCCCN(C)C[C@H]1Cc2cc(OC)c(OC)cc21]

and also to the application of this synthesis process in the preparation of ivabradine and of a key synthesis intermediate thereof.

Ivabradine of formula (II):

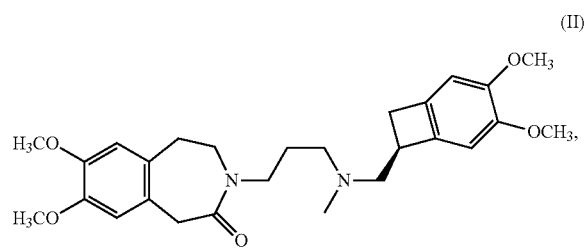 [SMILES: COc1cc2c(cc1OC)CC(=O)N(CCCN(C)C[C@H]1Cc3cc(OC)c(OC)cc31)CC2]
(II)

or 3-{3-[{[(7S)-3,4-dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one, and addition salts thereof with a pharmaceutically acceptable acid, and more especially the hydrochloride thereof, have very valuable pharmacological and therapeutic properties, especially bradycardic properties, which render those compounds useful in the treatment or prevention of various clinical conditions of myocardial ischaemia, such as angina pectoris, myocardial infarction and associated rhythm disorders, as well as in various pathologies involving rhythm disorders, especially supraventricular rhythm disorders, and in heart failure.

The preparation and therapeutic use of ivabradine and addition salts thereof with a pharmaceutically acceptable acid, and more especially the hydrochloride thereof, have been described in European patent specification EP 0 534 859.

That patent specification describes the synthesis of ivabradine hydrochloride starting from the compound of formula (III):

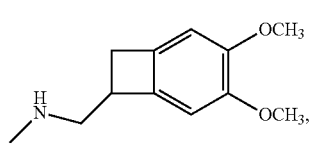
(III)

which is resolved to yield the compound of formula (IV):

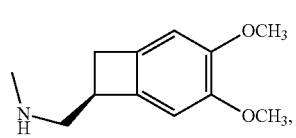
(IV)

which is reacted with the compound of formula (V):

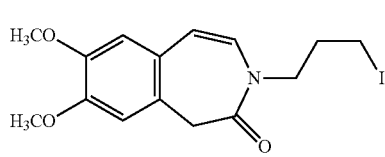
(V)

to yield the compound of formula (VI):

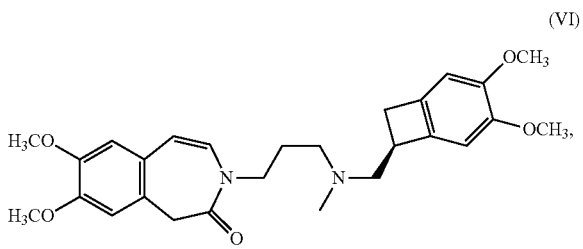 [SMILES: COc1cc2c(cc1OC)CC(=O)N(CCCN(C)C[C@H]1Cc3cc(OC)c(OC)cc31)C=C2]
(VI)

the catalytic hydrogenation of which yields ivabradine, which is then converted into its hydrochloride.

The disadvantage of the synthesis route described in EP 0 534 859 is that it yields ivabradine in a yield of only 1%.

The patent specification EP 0 534 859 also describes the preparation of the compound of formula (V), an intermediate in the synthesis of ivabradine, starting from 3-(3-chloropropyl)-7,8-dimethoxy-1,3-dihydro-2H-3-benzazepin-2-one.

For preparation of the 3-(3-chloropropyl)-7,8-dimethoxy-1,3-dihydro-2H-3-benzazepin-2-one, that patent specification refers to the publication of Reiffer M. et al. (J. Med. Chem. 1990; vol. 33 (5), pages 1496-1504). That publication describes the synthesis of that chlorinated compound starting from 7,8-dimethoxy-1,3-dihydro-2H-3-benzazepin-2-one.

In view of the pharmaceutical value of ivabradine, it is important to be able to obtain it using an effective synthesis process having a good yield.

It is also especially valuable to obtain good yields of 7,8-dimethoxy-1,3-dihydro-2H-3-benzazepin-2-one compounds, which are precursors of ivabradine.

The present invention relates to a process for the synthesis of the compound of formula (I):

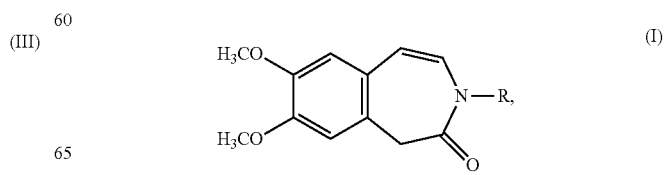
(I)

wherein R represents a para-methoxybenzyl (PMB) group or the following group:

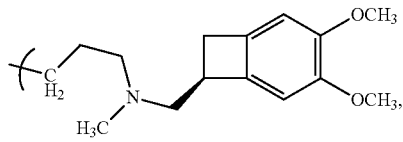 [SMILES: CCCCN(C)C[C@H]1Cc2cc(OC)c(OC)cc21]

characterised in that the compound of formula (VII):

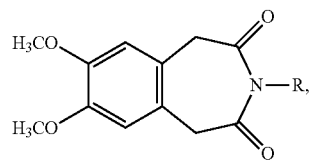

(VII)

wherein R is as defined hereinbefore,
is subjected to a reduction reaction,
in the presence of LiBH(Et)$_3$,
in an organic solvent,
to yield the compound of formula (I).

The amount of LiBH(Et)$_3$ used to carry out the reduction reaction on the compound of formula (VII) yielding the compound of formula (I) is preferably from 1 to 3 equivalents.

Among the organic solvents that may be used to carry out the reduction reaction on the compound of formula (VII) yielding the compound of formula (I), there may be mentioned, without implying any limitation, tetrahydrofuran (THF), methyl tetrahydrofuran (MeTHF), dichloromethane, toluene and diisopropyl ether.

The organic solvent used to carry out the reduction reaction on the compound of formula (VII) yielding the compound of formula (I) is preferably tetrahydrofuran.

The reduction reaction on the compound of formula (VII) yielding the compound of formula (I) is preferably performed at a temperature from −100° C. to 20° C.

When R represents the following group:

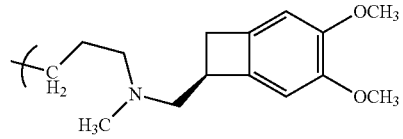 [SMILES: CCCCN(C)C[C@H]1Cc2cc(OC)c(OC)cc21]

the present invention relates also to a process for the synthesis of ivabradine,
characterised in that the compound of formula (VIII), a particular case of the compounds of formula (VII):

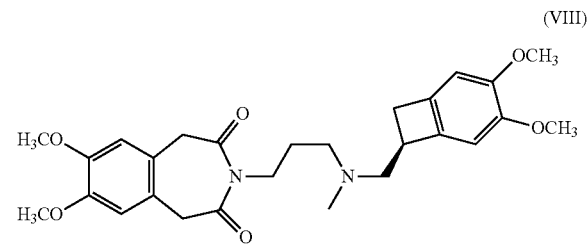 [SMILES: COc1cc2c(cc1OC)CC(=O)N(CCCN(C)C[C@H]1Cc3cc(OC)c(OC)cc31)C(=O)C2]

(VIII)

is subjected to a reduction reaction according to the process described hereinbefore to yield the compound of formula (VI), a particular case of the compounds of formula (I):

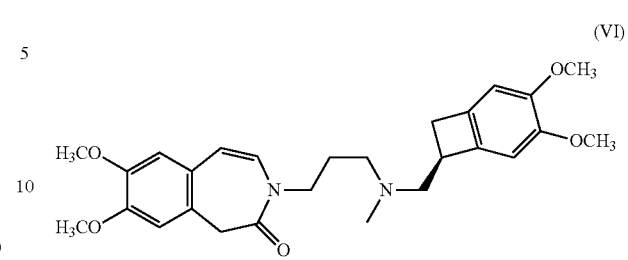

(VI)

and then the compound of formula (VI) is subjected to catalytic hydrogenation to yield ivabradine of formula (II):

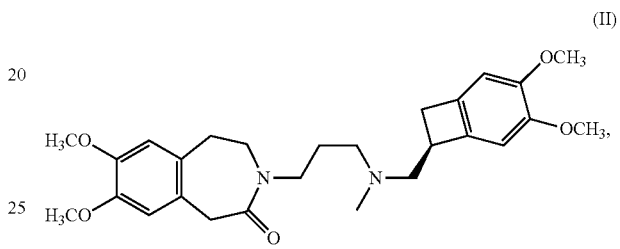

(II)

which may be converted into an addition salt thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into hydrates thereof.

The present invention relates also to a process for the synthesis of ivabradine starting from the compound of formula (VIII), characterised in that said compound of formula (VIII) is prepared starting from the compound of formula (IX):

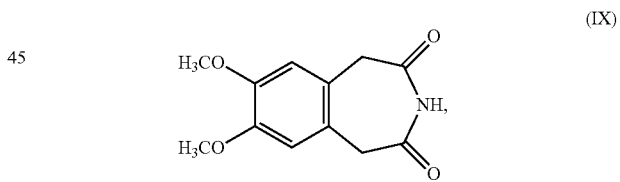

(IX)

which is reacted with the compound of formula (X):

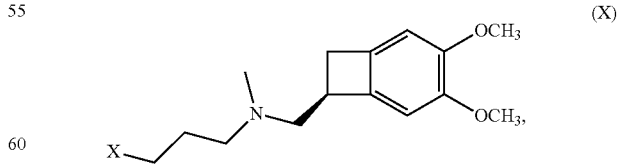

(X)

wherein X represents a halogen atom, a mesylate group or a tosylate group,
in the presence of a base,
in an organic solvent, to yield the compound of formula (VIII):

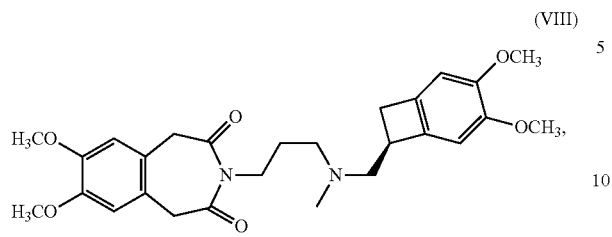

(VIII)

which is converted into the compound of formula (VI) in accordance with the process described hereinbefore, said compound of formula (VI) being converted into ivabradine of formula (II):

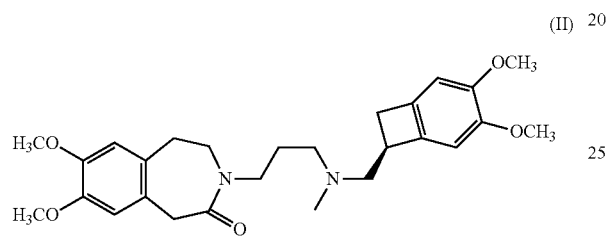

(II)

by the catalytic hydrogenation reaction described hereinbefore.

Among the bases that may be used to carry out the reaction between the compound of formula (IX) and the compound of formula (X), there may be mentioned, without implying any limitation, inorganic bases such as potassium carbonate, sodium carbonate, caesium carbonate, potassium hydrogen carbonate and sodium hydrogen carbonate, and organic bases such as triethylamine, diisopropylethylamine and pyridine.

The base used to carry out the reaction between the compound of formula (IX) and the compound of formula (X) is preferably potassium carbonate.

Among the organic solvents that may be used to carry out the reaction between the compound of formula (IX) and the compound of formula (X), there may be mentioned, without implying any limitation, acetonitrile, acetone, methyl ethyl ketone (MEK), dimethylformamide (DMF), N-methylpyrrolidone (NMP) and dimethyl sulphoxide (DMSO).

The organic solvent used to carry out the reaction between the compound of formula (IX) and the compound of formula (X) is preferably dimethylformamide (DMF).

The reaction between the compound of formula (IX) and the compound of formula (X) is preferably performed at a temperature from 20° C. to 150° C.

The present invention relates also to a process for the synthesis of ivabradine starting from the compound of formula (VIII), characterised in that said compound of formula (VIII) is prepared starting from the compound of formula (XI):

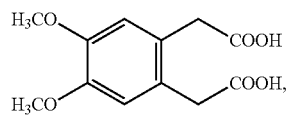

(XI)

which is converted into the compound of formula (XII):

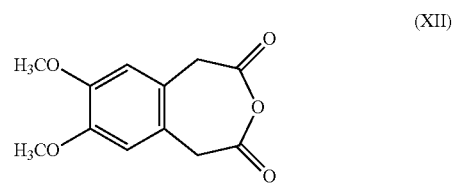 [SMILES: COc1cc2c(cc1OC)CC(=O)OC(=O)C2]

(XII)

by a cyclisation reaction in the presence of a coupling agent, in an organic solvent, said compound of formula (XII) then being reacted with the compound of formula (XIII):

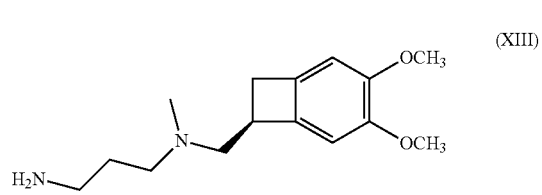 [SMILES: COc1cc2c(cc1OC)[C@@H](CN(C)CCCN)C2]

(XIII)

in the presence of a base, in an organic solvent, to yield the compound of formula (XIV):

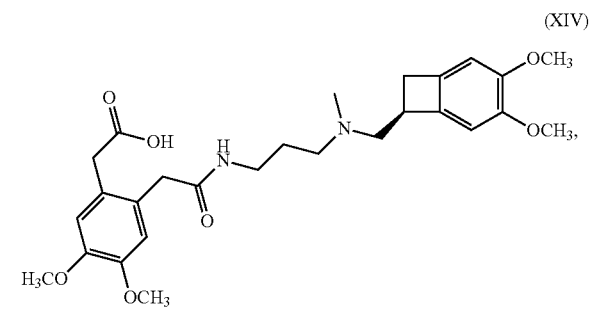 [SMILES: COc1cc(CC(=O)O)c(CC(=O)NCCCN(C)C[C@H]2Cc3cc(OC)c(OC)cc32)cc1OC]

(XIV)

which is subjected to a cyclisation reaction in the presence of a coupling agent, in an organic solvent, to yield the compound of formula (VIII):

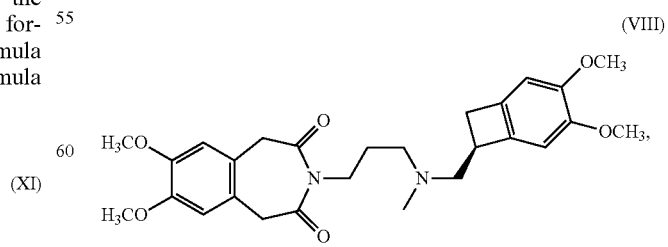

(VIII)

which is converted into the compound of formula (VI) in accordance with the process described hereinbefore, said compound of formula (VI) being converted into ivabradine of formula (II):

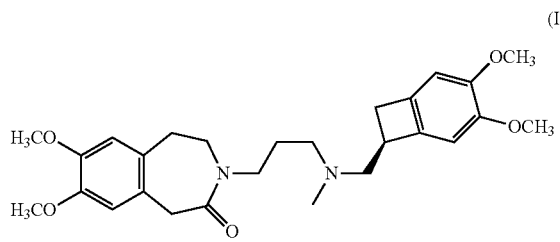

by the catalytic hydrogenation reaction described hereinbefore.

The compound of formula (XII) is preferably formed in situ, that is to say it is not isolated before being reacted with the compound of formula (XIII)

Among the coupling agents that may be used in the cyclisation reaction on the compound of formula (XI) yielding the compound of formula (XII), there may be mentioned, without implying any limitation, the following reagents: oxalyl chloride, thionyl chloride, N,N-dicyclohexylcarbodiimide (DCC), 1-ethyl-3-(3-dimethylaminopropyl)carbodiimide (EDCI), N,N-carbonyldiimidazole (CDI), 1-propanephosphonic acid cyclic anhydride (T3P) and 1-(methylsulphonyl)-1H-benzotriazole.

The coupling agent used in the cyclisation reaction on the compound of formula (XI) yielding the compound of formula (XII) is preferably thionyl chloride.

The amount of thionyl chloride used to carry out the cyclisation reaction on the compound of formula (XI) yielding the compound of formula (XII) is preferably from 1 to 5 equivalents.

Among the organic solvents that may be used to carry out the cyclisation reaction on the compound of formula (XI) yielding the compound of formula (XII), there may be mentioned, without implying any limitation, tetrahydrofuran (THF), methyl tetrahydrofuran (MeTHF), dichloromethane, toluene and diisopropyl ether.

The organic solvent used to carry out the cyclisation reaction on the compound of formula (XI) yielding the compound of formula (XII) is preferably toluene.

The cyclisation reaction on the compound of formula (XI) yielding the compound of formula (XII) is preferably performed at a temperature from 20° C. to 110° C.

Among the bases that may be used to carry out the reaction between the compound of formula (XII) and the compound of formula (XIII), there may be mentioned, without implying any limitation, inorganic bases such as potassium carbonate, sodium carbonate, caesium carbonate, potassium hydrogen carbonate and sodium hydrogen carbonate, and organic bases such as triethylamine, diisopropylethylamine and pyridine.

The base used in the reaction between the compound of formula (XII) and the compound of formula (XIII) is preferably triethylamine.

Among the organic solvents that may be used to carry out the reaction between the compound of formula (XII) and the compound of formula (XIII), there may be mentioned, without implying any limitation, tetrahydrofuran (THF), methyl tetrahydrofuran (MeTHF), dichloromethane, toluene and diisopropyl ether.

The organic solvent used to carry out the reaction between the compound of formula (XII) and the compound of formula (XIII) may also be composed of a mixture of two solvents from among the organic solvents mentioned hereinbefore.

The organic solvent used to carry out the reaction between the compound of formula (XII) and the compound of formula (XIII) is preferably a mixture of toluene and dichloromethane.

The reaction between the compound of formula (XII) and the compound of formula (XIII) is preferably performed at a temperature from 0° C. to 110° C.

Among the coupling agents that may be used to carry out the cyclisation reaction on the compound of formula (XIV), there may be mentioned, without implying any limitation, the following reagents: oxalyl chloride, thionyl chloride, N,N-dicyclohexylcarbodiimide (DCC), 1-ethyl-3-(3-dimethylaminopropyl)carbodiimide (EDCI), N,N-carbonyldiimidazole (CDI), 1-propanephosphonic acid cyclic anhydride (T3P) and 1-(methylsulphonyl)-1H-benzotriazole.

The coupling agent used to carry out the cyclisation reaction on the compound of formula (XIV) is preferably thionyl chloride.

The amount of thionyl chloride used to carry out the cyclisation reaction on the compound of formula (XIV) is preferably from 1 to 3 equivalents.

Among the organic solvents that may be used to carry out the cyclisation reaction on the compound of formula (XIV), there may be mentioned, without implying any limitation, tetrahydrofuran (THF), methyl tetrahydrofuran (MeTHF), dichloromethane, toluene and diisopropyl ether.

The organic solvent used to carry out the cyclisation reaction on the compound of formula (XIV) may also be composed of a mixture of two solvents from among the organic solvents mentioned hereinbefore.

The organic solvent used to carry out the cyclisation reaction on the compound of formula (XIV) is preferably a mixture of toluene and dichloromethane.

The cyclisation reaction on the compound of formula (XIV) is preferably performed at a temperature from 0° C. to 110° C.

When R represents a para-methoxybenzyl group, the present invention relates also to a process for the synthesis of the compound of formula (XV):

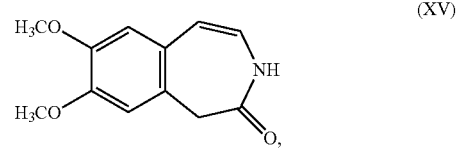 [SMILES: COc1cc2c(cc1OC)CC(=O)NC=C2]

characterised in that the compound of formula (XVI), a particular case of the compounds of formula (VII):

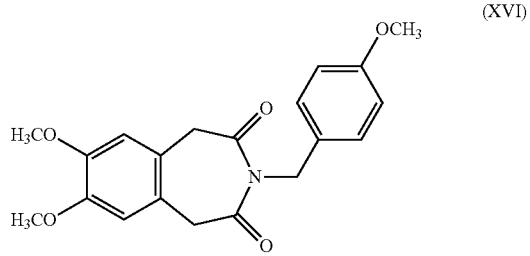 [SMILES: COc1ccc(CN2C(=O)Cc3cc(OC)c(OC)cc3CC2=O)cc1]

is subjected to a reduction reaction according to the process described hereinbefore, to yield the compound of formula (XVII), a particular case of the compounds of formula (I):

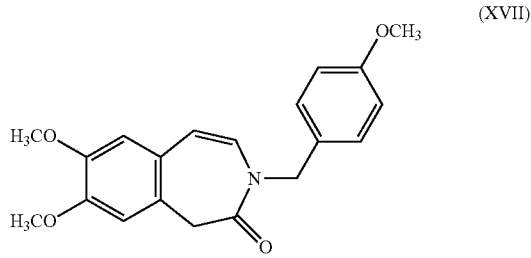 [SMILES: COc1ccc(CN2C=Cc3cc(OC)c(OC)cc3CC2=O)cc1]

and then the compound of formula (XVII) is deprotected to yield the compound of formula (XV).

Deprotection of the compound of formula (XVII) is preferably performed in trifluoroacetic acid at reflux.

The compound of formula (XV) is useful as an intermediate in the synthesis of ivabradine, as has been disclosed in the patent application EP 2 135 861.

The compounds of formulae (VIII) and (XIV) are new compounds, for use as synthesis intermediates in the chemical or pharmaceutical industry, especially in the synthesis of ivabradine, addition salts thereof with a pharmaceutically acceptable acid and hydrates thereof, and as such they form an integral part of the present invention.

List of Abbreviations Used:
DMF: dimethylformamide
IR: infrared
NMR: Nuclear Magnetic Resonance
m.p.: melting point
THF: tetrahydrofuran Flash chromatography on a silica column is carried out using an automated Buchi Sepacore chromatography apparatus.

The NMR spectra are recorded on a Bruker apparatus at 400 MHz for the proton spectra and at 100 MHz for the carbon spectra.

The chemical shifts are expressed in terms of ppm (internal standard: TMS).

The following abbreviations are used to describe the peaks: singlet (s), doublet (d), doublet of doublets (dd), triplet (t), quadruplet (q), multiplet (m).

The Examples hereinbelow illustrate the invention.

Preparation A

3-{3-[{[(7S)-3,4-dimethoxybicyclo[4.2.0]octa-1,3,5-trien-7-yl]methyl}(methyl)amino]-propyl}-7,8-dimethoxy-1H-3-benzazepine-2,4(3H,5H)-dione oxalate 5.9 g of 7,8-dimethoxy-1H-3-benzazepine-2,4(3H,5H)-dione (25.1 mmol), 7.1 g of 3-chloro-N-{[(7S)-3,4-dimethoxybicyclo[4.2.0]octa-1,3,5-trien-7-yl]methyl}-N-methylpropan-1-amine (25.1 mmol, 1 eq), 1.5 equivalents of $K_2CO_3$ (37.5 mmol), 0.2 equivalent of KI (5 mmol) and 60 mL of DMF are introduced into a reactor. The reaction mixture is heated at 80° C. for 2 hours, cooled to ambient temperature and then 90 mL of ice-cold water is introduced. The product is extracted with dichloromethane (2×60 mL). The organic phase is washed with 10% aqueous $NaHCO_3$ solution (60 mL) and then with saturated aqueous NaCl solution until the DMF has been removed.

After drying, the product is obtained in the form of an oil (11.4 g, 23.6 mmol), which is dissolved in ethyl acetate (34 mL). The mixture is heated to reflux and then a solution of oxalic acid (23.6 mmol) in ethanol (34 ml) is introduced. The mixture is cooled to ambient temperature, stirred for 2 hours and then filtered, and the filtrate is washed with ethanol (20 mL). The product in salt form is dried in a fan oven at 40° C.; 8.4 g of the title product are obtained in the form of a beige powder.

Yield: 57%

Analysis of the base:

$^1$H NMR (CDCl$_3$, 400 MHz): 1.59 ppm (2H, m)-1.61 ppm (2H, m)-2.16 ppm (3H, m)-2.39 ppm (1H, m)-2.60 ppm (3H, m)-3.13 ppm (1H, m)-3.22 ppm (2H, m)-3.28 ppm (1H, m)-3.36 ppm (1H, m)-3.66 ppm (3H, s)-3.67 ppm (3H, s)-3.68 ppm (3H, s)-3.69 ppm (3H, s)-3.71 ppm (2H, m)-6.64 ppm (1H, d)-6.68 ppm (1H, d)-6.71 ppm (1H, s)-6.81 ppm (1H, s).

$^{13}$C NMR (CDCl$_3$, 100 MHz): 26.24 ppm (CH$_2$)-27.55 ppm (CH$_2$)-36.38 ppm (CH$_2$)-39.16 ppm (CH$_2$)-41.54 ppm (CH$_2$)-41.58 ppm (CH)-42.90 ppm (CH$_3$)-56.54 ppm (CH$_2$)-56.56 ppm (CH$_3$)-56.70 ppm (CH$_3$)-56.98 ppm (CH$_3$)-57.03 ppm (CH$_3$)-63.15 ppm (CH$_2$)-108.63 ppm (CH)-109.30 ppm (CH)-115.34 ppm (CH)-115.73 ppm (CH)-127.08 ppm (C q)-128.15 ppm (C q)-136.66 ppm (C q)-140.30 ppm (C q)-149.60 ppm (C q)-149.76 ppm (C q)-150.99 ppm (C q)-151.57 ppm (C q)-173.35 ppm (C q)-173.95 ppm (C q)

Preparation B

{2-[2-({3-[{[(7S)-3,4-dimethoxybicyclo[4.2.0]octa-1,3,5-trien-7-yl]methyl}(methyl)-amino] propyl}amino)-2-oxoethyl]-4,5-dimethoxyphenyl}acetic acid 2.1 g of thionyl chloride (17.7 mmol, 1.6 eq) are added to a suspension of 2,2'-(4,5-dimethoxybenzene-1,2-diyl)diacetic acid (2.76 g, 10.9 mmol, 1 eq) in toluene (50 mL). The reaction mixture is heated to 80° C. and held at that temperature for 4 hours with stirring. A further charge of thionyl chloride (519 mg, 4.36 mmol) is added to the reaction mixture, held for 1 hour and then cooled to ambient temperature.

To the resulting solution there are added, at ambient temperature, triethylamine (3.31 g, 32.7 mmol, 3 eq) dissolved in dichloromethane (5 mL) and then a solution of N-{[(7S)-3,4-dimethoxybicyclo[4.2.0]octa-1,3,5-trien-7-yl]methyl}-N-methylpropane-1,3-diamine (2.87 g, 10.9 mmol, 1 eq) dissolved in dichloromethane (10 mL). After remaining in contact for 30 minutes, 6 mL of water are added, and the aqueous phase is acidified with 1N hydrochloric acid solution and extracted with dichloromethane (70 mL). After drying of the organic phase, the residue is purified by flash chromatography on a silica column (dichloromethane/methanol/triethylamine, proportions 80/20/0.1). 1.92 g of the title product are obtained in the form of a beige meringue.

Yield: 35%

$^1$H NMR (CDCl$_3$, 400 MHz): 1.62 ppm (2H, m)-2.26 ppm (3H, s)-2.44 (2H, m)-2.52 ppm (1H, dd)-2.65 ppm (1H, dd)-2.79 ppm (1H, m)-3.13 ppm (2H, m)-3.18 ppm (1H, dd)-3.44 ppm (2H, m)-3.46 ppm (2H, s)-3.49 ppm (2H, s)-3.72 ppm (2H, m)-3.73 ppm (3H, s)-3.74 ppm (3H, s)-3.77 ppm (3H, s)-6.59 ppm (1H, s)-6.63 ppm (1H, s)-6.67 ppm (1H, s)-6.72 ppm (1H, s)-7.62 ppm (NH, t).

$^{13}$C NMR (CDCl$_3$, 100 MHz): 26.1 ppm (CH$_2$)-35.5 ppm (CH$_2$)-37.7 ppm (CH$_2$)-39.6 ppm (CH$_3$)-40.7 ppm (CH$_2$)-41.5 ppm (CH)-42.1 ppm (CH$_2$)-55.1 ppm (CH$_2$)-55.8 ppm (CH$_3$)-55.9 ppm (CH$_3$)-56.2 (CH$_3$) ppm-56.3 ppm (CH$_3$)-60.9 ppm(CH$_2$)-106.7 ppm (CH)-107.4 ppm (CH)-112.7 ppm (CH)-113.7 ppm (CH)-126.5 ppm (C q)-128.6 ppm (C q)-134.7 ppm (C q)-137.6 ppm (C q)-147.6 ppm (C q)-147.8 ppm (C q)-149.5 ppm (C q)-150.1 ppm (C q)-172.3 ppm (C q)-178.2 ppm (C q).

Preparation C

3-{3-[{[(7S)-3,4-dimethoxybicyclo[4.2.0]octa-1,3,5-trien-7-yl]methyl}(methyl)amino]-propyl}-7,8-dimethoxy-1H-3-benzazepine-2,4(3H,5H)-dione Thionyl chloride (1.68 mmol, 1.68 eq) is added to a suspension of {2-[2-({3-[{[(7S)-3,4-dimethoxybicyclo[4.2.0]octa-1,3,5-trien-7-yl]methyl}(methyl)amino]propyl}amino)-2-oxo-ethyl]-4,5-dimethoxyphenyl}acetic acid (500 mg, 1 mmol) in a mixture of toluene/dichloromethane (15 ml, 66/33) at 60° C. After remaining in contact for 3 hours 30 minutes, 0.5 mmol of thionyl chloride dissolved in 5 mL of dichloromethane is added (0.5 eq). After remaining in contact for 1 hour 30 minutes, the reaction mixture is cooled to 25° C. 1N aqueous sodium hydroxide solution (10 mL) and dichloromethane (10 mL) are added to the mixture. The two phases are separated, and the organic phase is subjected to drying over sodium sulphate and is then dried. 0.38 g of a dark red oil is obtained. The product may be purified by flash chromatography on a silica column (eluant: dichloromethane/methanol 95/5).

Yield: 48%

$^1$H NMR (CDCl$_3$, 400 MHz): 1.59 ppm (2H, m)-1.61 ppm (2H, m)-2.16 ppm (3H, m)-2.39 ppm (1H, m)-2.60 ppm (3H, m)-3.13 ppm (1H, m)-3.22 ppm (2H, m)-3.28 ppm (1H, m)-3.36 ppm (1H, m)-3.66 ppm (3H, s)-3.67 ppm (3H, s)-3.68 ppm (3H, s)-3.69 ppm (3H, s)-3.71 ppm (2H, m)-6.64 ppm (1H, d)-6.68 ppm (1H, d)-6.71 ppm (1H, s)-6.81 ppm (1H, s).

$^{13}$C NMR (CDCl$_3$, 100 MHz): 26.24 ppm (CH$_2$)-27.55 ppm (CH$_2$)-36.38 ppm (CH$_2$)-39.16 ppm (CH$_2$)-41.54 ppm (CH$_2$)-41.58 ppm (CH)-42.90 ppm (CH$_3$)-56.54 ppm (CH$_2$)-56.56 ppm (CH$_3$)-56.70 ppm (CH$_3$)-56.98 ppm (CH$_3$)-57.03 ppm (CH$_3$)-63.15 ppm (CH$_2$)-108.63 ppm (CH)-109.30 ppm (CH)-115.34 ppm (CH)-115.73 ppm (CH)-127.08 ppm (C q)-128.15 ppm (C q)-136.66 ppm (C q)-140.30 ppm (C q)-149.60 ppm (C q)-149.76 ppm (C q)-150.99 ppm (C q)-151.57 ppm (C q)-173.35 ppm (C q)-173.95 ppm (C q).

Preparation D 7,8-dimethoxy-3-(4-methoxybenzyl)-1H-3-benzazepine-2,4(3H,5H)-dione 3 g of 7,8-dimethoxy-1H-3-benzazepine-2,4(3H,5H)-dione (12.8 mmol), 2 g of 4-methoxy-benzyl chloride (12.8 mmol, 1 eq), 2.64 g of K$_2$CO$_3$ (19.1 mmol, 1.5 eq), 1.06 g of KI (6.4 mmol, 0.5 eq) and 30 mL of acetonitrile are introduced into a 100-mL three-necked flask. The reaction mixture is heated at 80° C. for 3 hours 30 minutes. 1 g of 4-methoxybenzyl chloride is introduced three times and the reaction mixture is held at 80° C. for 24 hours. After returning to ambient temperature, 30 mL of water and 30 mL of dichloromethane are introduced. After extraction and drying of the organic phase, the dark red oil obtained is purified by flash chromatography on a silica column (eluant: dichloromethane/methanol 99/1) to obtain the title product.

Yield: 52%

$^1$H NMR (CDCl$_3$, 400 MHz): 3.73 ppm (3H, s)-3.85 ppm (6H, s)-4.01 ppm (4H, s)-4.85 ppm (2H, s)-6.77 ppm (4H, m)-7.20 ppm (2H, d).

$^{13}$C NMR (CDCl$_3$, 100 MHz): 44.71 ppm (2 CH$_2$)-45.08 ppm (CH$_2$)-55.18 ppm (CH$_3$)-56.11 ppm (2 CH$_3$)-111.80 ppm (2 CH)-113.60 ppm (2 CH)-123.64 ppm (2 C q)-129.69 ppm (C q)-130.01 ppm (2 CH)-148.75 ppm (2 C q)-158.75 ppm (C q)-170.82 ppm (2 C q).

EXAMPLE 1

3-{3-[{[(7S)-3,4-dimethoxybicyclo[4.2.0]octa-1,3,5-trien-7-yl]methyl}(methyl)amino]-propyl}-7,8-dimethoxy-1,3-dihydro-2H-3-benzazepin-2-one A solution of 3-{3-[{[(7S)-3,4-dimethoxybicyclo[4.2.0]octa-1,3,5-trien-7-yl]methyl}(methyl)-amino]propyl}-7,8-dimethoxy-1H-3-benzazepine-2,4(3H,5H)-dione (0.47 g, 0.97 mmol) in THF (10 mL) is cooled to −78° C. LiBH(Et)$_3$ (1.3 g, 1.46 mmol, 1.5 eq, as a 1M solution in THF) is then slowly added to the reaction mixture. After 1 hour at −78° C., 15 mL of 1N HCl are added to the mixture. The reaction mixture slowly comes back to ambient temperature, where it is held for 18 hours. The product is extracted with dichloromethane (2×10 mL). The organic phase is dried over sodium sulphate and then evaporated. After purification by flash chromatography on a silica column (eluant: dichloromethane/methanol 9/1), 180 mg of expected product are obtained.

Yield: 34%

$^1$H NMR (CDCl$_3$, 400 MHz): 1.72 ppm (2H, m)-2.27 ppm (3H, s)-2.33 ppm (2H, t)-2.50 ppm (1H, dd)-2.65 ppm (1H, m)-2.67 ppm (1H, dd)-3.21 ppm (1H, dd)-3.44 ppm (2H, s)-3.47 ppm (1H, m)-3.61 ppm (2H, m)-3.85 ppm (3H, s)-3.86 ppm (6H, s)-3.90 ppm (3H, s)-6.23 ppm (1H, d)-6.32 ppm (1H, d)-6.70 ppm (1H, s)-6.71 ppm (2H, s)-6.79 ppm (1H, s).

$^{13}$C NMR (CDCl$_3$, 100 MHz): 26.3 ppm (CH$_2$)-35.1 ppm (CH$_2$)-40.7 ppm (CH)-42.4 ppm (CH$_3$)-43.3 ppm (CH$_2$)-46.2 ppm (CH$_2$)-54.7 ppm (CH$_2$)-55.9 ppm (CH$_3$)-56.2 ppm (CH$_3$)-56.3 ppm (CH$_3$)-61.9 ppm (CH$_3$)-106.7 ppm (CH)-107.4 ppm (CH)-109.4 ppm (CH)-111.2 ppm (CH)-117.0 ppm (CH)-124.8 ppm (C q)-126.4 ppm (C q)-128.7 ppm (CH)-135.0 ppm (C q)-139.1 ppm (C q)-148.0 ppm (C q)-149.3 ppm (C q)-149.7 ppm (C q)-149.8 ppm (C q)-167.6 ppm (C q).

EXAMPLE 2

3-{3-[{[(7S)-3,4-dimethoxybicyclo[4.2.0]octa-1,3,5-trien-7-yl]methyl}(methyl)amino]-propyl}-7,8-dimethoxy-1,3,4,5-tetrahydro-2H-3-benzazepin-2-one In a 250-ml autoclave, 4 g of the product obtained in Example 1 and 2 g of Pd(OH)$_2$ (20%, 50% moist) are added to a solution of ethanol (90 mL) and acetic acid (10 mL). After remaining in contact for 5 hours at ambient temperature under a hydrogen pressure of 5 bar, the reaction mixture is filtered over Celite®. The residue obtained after concentrating under reduced pressure is taken up in dichloromethane (100 mL) and then washed with saturated aqueous sodium bicarbonate solution. The oil obtained after drying the organic phase over MgSO$_4$ and then concentrating under reduced pressure is purified by chromatography over silica (dichloromethane/ethanol/NH$_4$OH 28%: 95/5/0.5), and 2.6 g of the title product are obtained in the form of an oil.

Yield: 74%

IR (pure): σ=2788, 1646, 1519–1461, 1245–1105 cm$^{-1}$.

EXAMPLE 3

7,8-dimethoxy-3-(4-methoxybenzyl)-1,3-dihydro-2H-3-benzazepin-2-one 1 g of LiBH(Et)$_3$ (1.12 mmol, 1.33 eq, 1M solution in THF) is added to a solution of 7,8-dimethoxy-3-(4-methoxybenzyl)-1H-3-benzazepine-2,4(3H,5H)-dione (300 mg, 0.84 mmol) in THF (4.5 mL) at −78° C. The reaction mixture is held at that temperature for 1 hour 30 minutes with stirring and then hydrolysed with saturated aqueous ammonium chloride solution (4 mL). After a slow return to ambient temperature, 2 mL of water and 5 mL of dichloromethane are introduced, the aqueous phase is extracted with 10 mL of dichloromethane, and the organic phase is dried. The crude product obtained is purified by flash chromatography on a silica column (dichloromethane/methanol 98/2) to obtain the title product.

Yield: 63%

$^1$H NMR (CDCl$_3$, 400 MHz): 3.48 ppm (2H, s)-3.75 ppm (3H, s)-3.85 ppm (3H, s)-3.89 ppm (3H, s)-4.67 ppm (2H, s)-6.18 ppm (1H, d)-6.29 ppm (1H, d)-6.68 ppm (1H, s)-6.79 ppm (1H, s)-6.80 ppm (2H, d)-7.05 ppm (2H, d).

$^{13}$C NMR (CDCl$_3$, 100 MHz): 43.20 ppm (CH$_2$)-50.18 ppm (CH2)-55.22 ppm (CH$_3$)-55.94 ppm (2 CH$_3$)-109.42 ppm (CH)-111.19 ppm (CH)-113.94 ppm (2CH)-117.30 ppm (CH)-124.63 ppm (C q)-126.41 ppm (C q)-127.86 ppm (1CH)-128.65 ppm (C q)-128.96 ppm (2CH)-147.95 ppm (C q)-149.82 ppm (C q)-158.92 ppm (C q)-167.90 ppm (C q).

EXAMPLE 4

7,8-dimethoxy-3-dihydro-2H-3-benzazepin-2-one 640 mg (1.89 mmol) of 7,8-dimethoxy-3-(4-methoxybenzyl)-1,3-dihydro-2H-3-benzazepin-2-one are refluxed in 4 mL of trifluoroacetic acid. After remaining in contact for 8 hours, 8 mL of demineralised water are added and the reaction mixture is filtered. The precipitate obtained is washed successively with 4 mL of demineralised water and then twice with 4 mL of methanol to obtain, after drying, 401 mg of a green powder corresponding to the title product.

Yield: 97% m.p.: 236° C.

$^1$H NMR (CDCl$_3$, 400 MHz): 3.42 ppm (2H, s)-3.86 ppm (3H, s)-3.88 ppm (3H, s)-6.17 ppm (1H, m)-6.29 ppm (1H, d)-6.70 ppm (1H, s)-6.75 ppm (1H, s)-7.68 ppm (NH).

$^{13}$C NMR (CDCl$_3$, 100 MHz): 42.65 ppm (CH$_2$)-55.97 ppm (2 CH$_3$)-109.78 ppm (CH)-111.48 ppm (CH)-116.89 ppm (CH)-122.69 ppm (CH)-123.56 ppm (C q)-126.77 ppm (C q)-148.11 ppm (C q)-149.87 ppm (C q)-170.18 ppm (C q)/

The invention claimed is:

1. A process for the synthesis of a compound of formula (I):

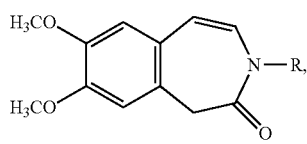

(I)

wherein R represents a para-methoxybenzyl (PMB) group or the following group:

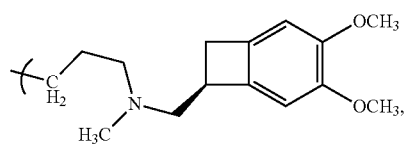

wherein a compound of formula (VII):

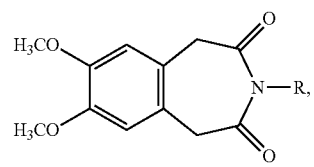

(VII)

wherein R is as defined hereinbefore, is subjected to a reduction reaction, in the presence of LiBH(Et)$_3$, in an organic solvent, to yield the compound of formula (I).

2. The process according to claim 1, wherein the amount of LiBH(Et)$_3$ used to carry out the reduction reaction on the compound of formula (VII) yielding the compound of formula (I) is from 1 to 3 equivalents.

3. The process according to claim 1, wherein the organic solvent used to carry out the reduction reaction on the compound of formula (VII) yielding the compound of formula (I) is selected from the group consisting of tetrahydrofuran (THF), methyl tetrahydrofuran (MeTHF), dichloromethane, toluene and diisopropyl ether.

4. The process according to claim 3, wherein the organic solvent used to carry out the reduction reaction on the compound of formula (VII) yielding the compound of formula (I) is tetrahydrofuran.

5. The process according to claim 1, wherein the reduction reaction on the compound of formula (VII) yielding the compound of formula (I) is performed at a temperature from −100° C. to 20° C.

6. A process for the synthesis of ivabradine, wherein a compound of formula (VIII):

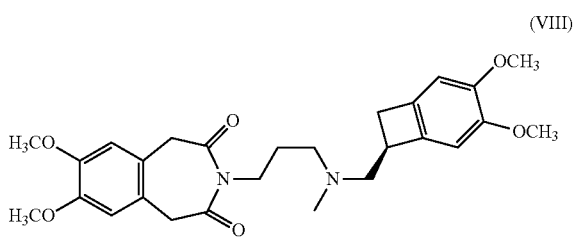 [SMILES: COc1cc2c(cc1OC)CC(=O)N(CCCN(C)C[C@H]1Cc3cc(OC)c(OC)cc31)C(=O)C2]

(VIII)

is subjected to a reduction reaction according to claim 1 to yield a compound of formula (VI),:

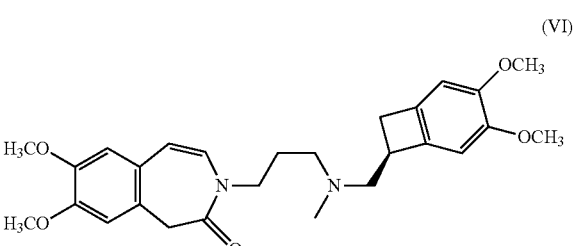

(VI)

which compound of formula (VI) is subjected to catalytic hydrogenation to yield ivabradine of formula (II):

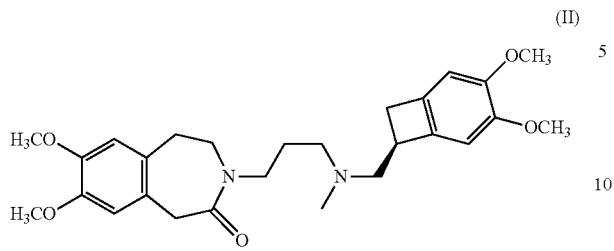

which may be converted into an addition salt thereof with a pharmaceutically acceptable acid selected from hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid, and into hydrates thereof.

7. The process according to claim 6, wherein the compound of formula (VIII) is prepared starting from a compound of formula (IX):

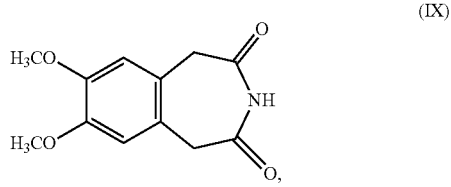 [SMILES: COc1cc2c(cc1OC)CC(=O)NC(=O)C2]

which is reacted with a compound of formula (X):

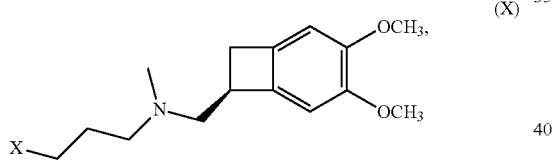

wherein X represents a halogen atom, a mesylate group or a tosylate group,
in the presence of a base,
in an organic solvent,
to yield the compound of formula (VIII):

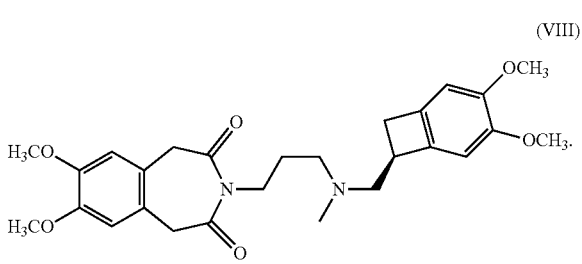 [SMILES: COc1cc2c(cc1OC)CC(=O)N(CCCN(C)C[C@H]1Cc3cc(OC)c(OC)cc31)C(=O)C2]

8. The process according to claim 6, wherein the compound of formula (VIII) is prepared starting from a compound of formula (XI):

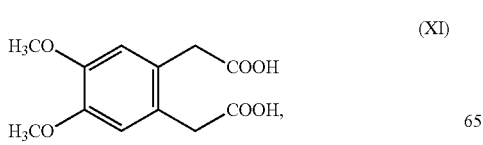

which is converted into a compound of formula (XII):

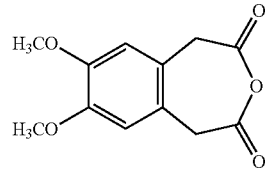

in the presence of a coupling agent,
in an organic solvent,
which compound of formula (XII) is then reacted with a compound of formula (XIII):

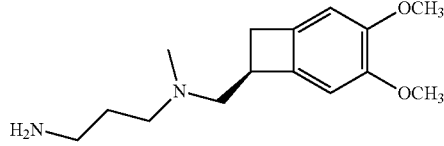

in the presence of a base,
in an organic solvent,
to yield a compound of formula (XIV):

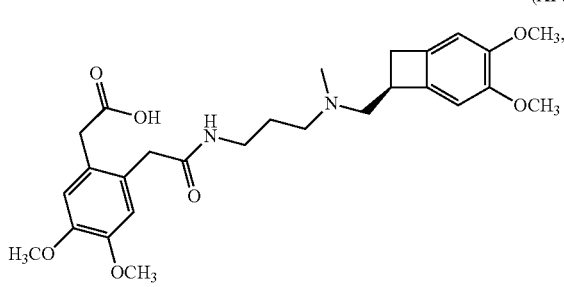

which is subjected to a cyclisation reaction in the presence of a coupling agent,
in an organic solvent,
to yield the compound of formula (VIII):

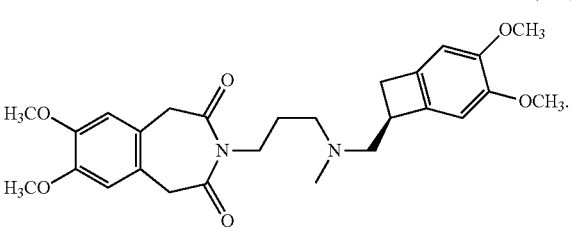

9. A process for preparation of a compound of formula (XV):

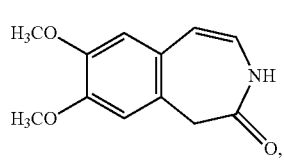

wherein a compound of formula (XVI):
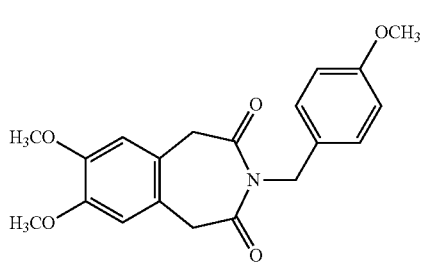
is subjected to a reduction reaction according to claim 1 to yield a compound of formula (XVII):
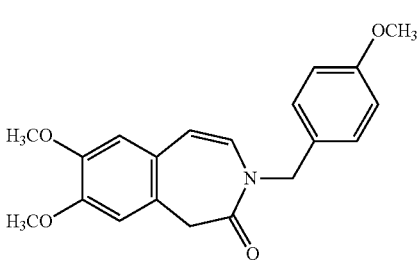
which compound of formula (XVII) is deprotected to yield the compound of formula (XV).
10. A compound of formula (VIII):
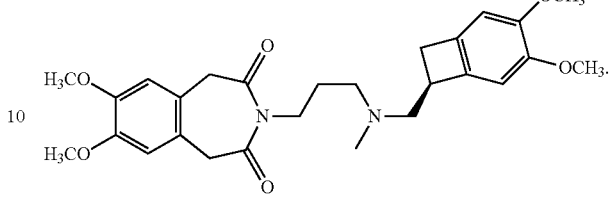
11. A compound of formula (XIV):
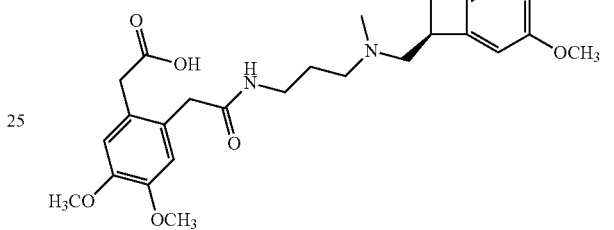
* * * * *

UNITED STATES PATENT AND TRADEMARK OFFICE
CERTIFICATE OF CORRECTION

| | | |
|---|---|---|
| PATENT NO. | : 8,927,708 B2 | Page 1 of 1 |
| APPLICATION NO. | : 14/223143 | |
| DATED | : January 6, 2015 | |
| INVENTOR(S) | : Alexandre Le Flohic | |

It is certified that error appears in the above-identified patent and that said Letters Patent is hereby corrected as shown below:

On The Title Page, item (56) Foreign Patent Documents: "WO 2008/066681" should be --WO 2008/065681--.

Signed and Sealed this
Twenty-eighth Day of April, 2015

Michelle K. Lee
*Director of the United States Patent and Trademark Office*